US008097013B2

(12) United States Patent
Oki et al.

(10) Patent No.: US 8,097,013 B2
(45) Date of Patent: *Jan. 17, 2012

(54) SKIN INCISION INSTRUMENT AND METHOD FOR INCISING SKIN WITH THE SAME

(75) Inventors: Akio Oki, Kyoto (JP); Hiroaki Oka, Osaka (JP)

(73) Assignee: Panasonic Corporation, Osaka (JP)

( * ) Notice: Subject to any disclaimer, the term of this patent is extended or adjusted under 35 U.S.C. 154(b) by 59 days.

This patent is subject to a terminal disclaimer.

(21) Appl. No.: 12/827,472

(22) Filed: Jun. 30, 2010

(65) Prior Publication Data

US 2010/0268259 A1 Oct. 21, 2010

Related U.S. Application Data

(63) Continuation of application No. 12/699,538, filed on Feb. 3, 2010, now Pat. No. 7,833,173, which is a continuation of application No. PCT/JP2009/002020, filed on May 8, 2009.

(30) Foreign Application Priority Data

May 13, 2008 (JP) ................................. 2008-125542

(51) Int. Cl.
*A61B 17/34* (2006.01)

(52) U.S. Cl. .......................... 606/181; 600/573; 600/583

(58) Field of Classification Search .................. 600/573, 600/578, 579, 583, 584; 606/181–183
See application file for complete search history.

(56) References Cited

U.S. PATENT DOCUMENTS 5,423,847 A * 6/1995 Strong et al. .................. 606/182
5,613,978 A 3/1997 Harding
(Continued)

FOREIGN PATENT DOCUMENTS

JP 08-168478 7/1996
(Continued)

OTHER PUBLICATIONS

United States Office Action issued in U.S. Appl. No. 12/683,574, mailed on Mar. 10, 2010.
(Continued)

*Primary Examiner* — Max Hlndenburg
*Assistant Examiner* — Michael C Stout
(74) *Attorney, Agent, or Firm* — McDermott Will & Emery LLP

(57) ABSTRACT

Provided are skin incision instrument to efficiently incise minimal portions and a method for incising skin with the skin incision instrument. The skin incision instrument according to the present invention comprises a holder, a needle, a needle drive unit, two or more skin expander sets, and a reader, wherein the skin expander sets comprise a first skin expander and a second skin expander; the first skin expander and the second skin expander are capable of expanding skin at both sides of the linear incision portion away from the linear incision portion and expanding the linear incision portion in a direction to expand the linear incision portion; and, minimal portions are efficiently incised by selecting a single skin expander set from two or more of the skin expander set based on the direction of the linear incision portion, such that an angle is adjusted to 45 degrees or more and 90 degrees or less wherein the angle is formed by the direction of the linear incision portion read by the reader and the direction to expand the skin by the single skin expander set.

8 Claims, 11 Drawing Sheets

U.S. PATENT DOCUMENTS

| | | | |
|---|---|---|---|
| 5,857,983 | A | 1/1999 | Douglas et al. |
| 5,879,311 | A | 3/1999 | Duchon et al. |
| 5,951,492 | A | 9/1999 | Douglas et al. |
| 5,951,493 | A | 9/1999 | Douglas et al. |
| 6,015,392 | A | 1/2000 | Douglas et al. |
| 6,048,352 | A | 4/2000 | Douglas et al. |
| 6,056,701 | A | 5/2000 | Duchon et al. |
| 6,099,484 | A | 8/2000 | Douglas et al. |
| 6,183,489 | B1 | 2/2001 | Douglas et al. |
| 6,319,210 | B1 | 11/2001 | Douglas et al. |
| 6,332,871 | B1 | 12/2001 | Douglas et al. |
| 6,352,514 | B1 | 3/2002 | Douglas et al. |
| 6,537,242 | B1 | 3/2003 | Palmer |
| 7,201,723 | B2 | 4/2007 | Chan |
| 7,235,056 | B2 | 6/2007 | Duchon et al. |
| 7,351,213 | B2* | 4/2008 | Wong et al. ............... 600/584 |
| 7,377,903 | B2 | 5/2008 | Raney |
| 2002/0002344 | A1 | 1/2002 | Douglas et al. |
| 2002/0010406 | A1 | 1/2002 | Douglas et al. |
| 2002/0049459 | A1 | 4/2002 | Kato |
| 2002/0082522 | A1 | 6/2002 | Douglas et al. |
| 2002/0188223 | A1* | 12/2002 | Perez et al. ............... 600/573 |
| 2004/0059256 | A1 | 3/2004 | Perez |
| 2006/0155317 | A1* | 7/2006 | List ............... 606/181 |
| 2006/0173379 | A1 | 8/2006 | Rasch-Menges et al. |
| 2007/0060845 | A1 | 3/2007 | Perez |
| 2008/0294064 | A1 | 11/2008 | Calasso et al. |

FOREIGN PATENT DOCUMENTS

| | | |
|---|---|---|
| JP | 10-508527 | 8/1998 |
| JP | 2001-524343 | 12/2001 |
| JP | 2002-502271 | 1/2002 |
| JP | 2002-125976 | 5/2002 |
| JP | 2003-102712 | 4/2003 |
| JP | 2003-534881 | 11/2003 |
| JP | 2005-507733 | 3/2005 |
| JP | 2006-014789 | 1/2006 |
| JP | 2006-075369 | 3/2006 |
| WO | WO 97/42882 | 11/1997 |
| WO | WO 97/42885 | 11/1997 |
| WO | WO 99/027852 | 6/1999 |
| WO | WO 01/93931 A1 | 12/2001 |
| WO | WO 02/100275 A1 | 12/2002 |
| WO | WO 2007/054335 A2 | 5/2007 |

OTHER PUBLICATIONS

United States Notice of Allowance issued in U.S. Appl. No. 12/699,538, mailed Sep. 8, 2010.

* cited by examiner

SKIN INCISION INSTRUMENT AND METHOD FOR INCISING SKIN WITH THE SAME

RELATED APPLICATIONS

This application is a continuation of U.S. patent application Ser. No. 12/699,538, filed on Feb. 3, 2010 now U.S. Pat. No. 7,833,173, which is a continuation application under U.S.C 111(a) of pending prior International application No. PCT/JP2009/002020, filed on May 8, 2009, which in turn claims the benefit of Japanese Application No. 2008-125542 filed on May 13, 2008, the disclosures of which Application applications are incorporated by reference herein.

TECHNICAL FIELD

The present invention relates to an instrument to efficiently incise skin and an incising method with the same.

BACKGROUND ART

Blood test has conventionally been employed as an important tool to monitor health condition, postoperative course, and medication effects in the subjects. For example, glucose level management is an essential for hyperglycemic patients. Then, when an insulin infusion is performed, the glucose level management after each meal has also to be performed under supervision of physician in addition to the conventional glucose level management prior to each meal and bed time.

Recent years, the glucose level management can be performed without significantly changing the daily life by performing self glucose determination at home or office. About 200 μm of scratch is made at fingertip with small puncture device called as Lancet and several μL of blood are collected. Then, glucose level is determined by applying the blood so collected onto small sensor. This is a typical glucose determination method.

However, excruciating pain was generated at the collecting of the blood, and it was unacceptable physical pain and emotional distress for the subjects. Accordingly, a method for collecting blood with less physical damage has been desired.

As one means to solve this problem, there is a device which allows smooth collection of blood by forming minimum incision portion and opening it with pressure or tension applied around the incision portion.

According to such device, a needle with blade surface at the tip thereof is punctured into the skin. FIG. 17 shows a general puncture needle. The general needle has three polished surfaces at its tip. FIGS. 18 (a)-(c) illustrate how an incision portion is formed by puncturing the needle into the skin. FIG. 18 (a) illustrates how a tip of the needle is slightly punctured into the skin. Then, FIG. 18 (b) illustrates how the incision portion is expanded by deeply puncturing into the skin tip of the needle. Finally, FIG. 18 (c) illustrates how the skin at both sides of the incision portion is approached by removing the needle from skin.

There is a conventional skin incision instrument to form the incision portion as illustrated in FIG. 18 (c).

For example, according to Patent Publication 1, a blood collection device with needle is positioned onto the skin and it is pressed downwardly thereat. The blood collection device comprises a skin expander unit, and then uniform puncture for the skin can be realized by expanding the skin in the target area under the blood collection device with the skin expander unit. As a result thereof, the blood can be collected with less physical damage.

Patent Publication 2 discloses a vessel surgery device for professional use. The vessel surgery device comprises the vessel support which holds a part of the vessel and the incision device which incises the vessel. The vessel support comprises a pair of arms and needles mounted respectively around the tip of the arm, and it can support the vessel by puncturing the needles into the vessels. Further, by rotating the turn buckle mounted between the both arms, the arms would be opened and be shut, thereby, the space between both needles is adjusted and such state can be maintained. Then, by pressing a manual operation button of the incision device, blade was inserted between both needles, and the blood vessels can be incised thereby.

Patent Publication 3 discloses a skin incision instrument which can easily collect blood by incising a part of skin with a needle, pressing downwardly a skin stimulator after the needle is removed from the incision portion, and forming the incision portion.

Particulars of the skin incision instrument disclosed in Patent Publication 3 are as follows. FIG. 19 and FIG. 20 illustrate an overall view and an enlarged view of the skin incision instrument, respectively. Identical symbols are denoted for the identical elements between FIG. 19 and FIG. 20. As illustrated in FIG. 19 and FIG. 20, first of all, the incision instrument 10 is pressed to the skin 13. Inside of the incision instrument 10 comprises the lever 18, and the skin 13 is pressed downwardly by pushing down the lever 18 inwardly. Thereby, the blood is collected by expanding the skin 13 and forming the incision portion 19. In addition, the collection of blood is promoted by heating or vibrating the lever 18.

CITATION LIST

Patent Literature

Patent Publication 1: Japanese Patent Laid-Open Publication No. 2003-534881 (Page 27, FIG. 11)
Patent Publication 2: Japanese Patent Laid-Open Publication No. 2002-125976 (Page 16, FIG. 15)
Patent Publication 3: Japanese Patent Laid-Open Publication No. 2003-102712 (Page 8, FIG. 17)
Patent Publication 4: Japanese Patent Laid-Open Publication No. 2001-524343 (Paragraph of 0026)
Patent Publication 5: Japanese Patent Laid-Open Publication No. Hei8-168478

SUMMARY OF INVENTION

Technical Problem

However, the incision portion 19 can not always be formed by merely pressing the skin according to the conventional method. In particular, when the longitudinal length of the incision portion 19 is microscale length, the incision portion 19 can not often be formed.

Namely, when the length of the incision portion is as small as the microscale length such as the height of ridge line in fingerprint of finger pad (about 100 μm), the space between such ridge lines (about 350 μm), or the depth of shallow wrinkles (about 200-300 μm), the form of the incision portion is changed to various forms including a straight line, a curve line and a wavy line.

As stated above, when the direction of the incision portion is changed to various forms including a straight line, a curve line and a wavy line, there was no available method in the prior arts except for expanding skin at the predetermined direction without taking the direction of the incision portion into consideration or expanding skin at the isotropic direction. Accordingly, when the direction of the incision portion is changed variously, there is a problem that the skin tends to be expanded to the direction of closing the incision portion rather than the direction of opening the same.

The purpose of the present invention is to solve such problems known in the prior arts and to provide the skin incision instrument which is capable of efficiently incising the skin regardless of various directions of the incision portion including a straight line, a curve line and a wavy line. The other purpose of the present invention is to provide a method for incising skin with the skin incision instrument.

Solution to Problem

In order to eliminate such problems known in the prior arts, the present inventions directed to a skin incision instrument comprising:
- a holder (101);
- a needle (102);
- a needle drive unit (105);
- n (n is a natural number of two or more) skin expander sets (106); and
- a reader (109); wherein
- the needle (102) and the skin expander (106) are mounted at an end of the holder (101),
- the needle drive unit (105) is mounted in the holder (101),
- the needle drive unit (105) is capable of forming linear incision portion (402) in a skin caused to contact with the end of the holder (101) by moving the needle (102),
- each of the skin expander sets (106) comprises a first skin expander (107a) and a second skin expander (107b),
- the first skin expander (107a) and the second skin expander (107b) are positioned around the needle (102) wherein the needle (102) is as a symmetry axis,
- the first skin expander (107a) and the second skin expander (107b) are capable of expanding skin at both sides of the linear incision portion (402) (namely, the skin sandwiching the incision portion) away from the linear incision portion (402) and expanding the linear incision portion in a direction to expand the linear incision portion (402),
- the reader (109) is capable of reading the direction of the linear incision portion (402), and
- m (m is a natural number of one or more, and n>m) skin expander set(s) is/are selectable from n skin expander sets (106) based on the direction of the linear incision portion (402) read by the reader (109), such that an angle is adjusted to 45 degrees or more and 90 degrees or less wherein the angle is formed by the direction of the linear incision portion (402) read by the reader 109 and the direction to expand the skin by the m skin expander sets (106).

The skin expander sets preferably operate in association with the reader.

The reader preferably comprises an imaging unit, a light source, and a calculating unit.

The reader preferably comprises a mechanism which operates in association with the skin expander sets to read a direction of the linear incision portion.

The holder preferably comprises a mark indicating a direction of the blade surface.

A blood test kit comprising the foregoing skin incision instrument is also fallen within the scope of the present invention.

Then, in order to eliminate such problems known in the prior arts, the present inventions directed to a method for incising skin with a skin incision instrument comprising:
- a holder (101);
- a needle (102);
- a needle drive unit (105);
- n (n is a natural number of two or more) skin expander sets (106); and
- a reader (109); wherein
- the needle (102) and the skin expander (106) are mounted at an end of the holder (101),
- the needle drive unit (105) is mounted in the holder (101),
- the needle drive unit (105) is capable of forming linear incision portion (402) in a skin caused to contact the end of the holder (101) by moving the needle (102),
- each of the skin expander sets (106) comprises a first skin expander (107a) and a second skin expander (107b),
- the first skin expander (107a) and the second skin expander (107b) are positioned around the needle (102) which is a symmetry axis,
- the first skin expander (107a) and the second skin expander (107b) are capable of expanding skin at both sides of the linear incision portion (402) (namely, the skin sandwiching the incision portion) away from the linear incision portion (402) and expanding the linear incision portion in a direction to expand the linear incision portion (402), and
- the reader (109) is capable of reading a direction of the linear incision portion (402), and
- the method comprises the steps of:
- incision portion forming step of forming linear incision portion (402) in a skin caused to contact the end of the holder (101) by moving the needle (102) with the needle drive unit (105),
- reading step of reading a direction of the linear incision portion (402) with the reader (109),
- selecting step of selecting m (m is a natural number of one or more, and n>m) skin expander set(s) from n skin expander sets (106) based on the direction of the linear incision portion (402) read in the reading step, such that an angle is adjusted to 45 degrees or more and 90 degrees or less wherein the angle is formed by the direction of the linear incision portion (402) read by the reader (109) and the direction to expand the skin by the m skin expander set(s) (106), and
- skin expanding step of expanding the skin at both sides of the linear incision portion (402) away from the linear incision portion (402) with the m skin expander set(s) (106).

Preferably, m is one.

The skin incision instrument according to the present invention preferably further comprises a calculating unit, and in the selecting step, the calculating unit selects m skin expander set(s) from n skin expander sets (106) based on the direction of the linear incision portion (402) read in the reading step, such that an angle is adjusted to 45 degrees or more and 90 degrees or less wherein the angle is formed by the direction of the linear incision portion (402) read by the reader (109) and the direction to expand the skin by the m skin expander set(s) (106).

These and other objects, additional aspects and advantages of the present invention will become apparent from the following detailed description on the preferred embodiments by referring to the drawings attached hereto.

Advantageous Effects of Invention

According to the skin incision instrument of the present invention and the method for incising skin with the same, since the direction to expand the skin is capable of easily being defined in the direction of incision portion, incision portions are capable of efficiently being formed even if the direction of the incision portion is changed variously into forms including a straight line, a curve line and a wavy line.

DESCRIPTION OF EMBODIMENTS

Embodiments of the present invention are described as follows with reference to the drawings attached hereto.

Figure 1:
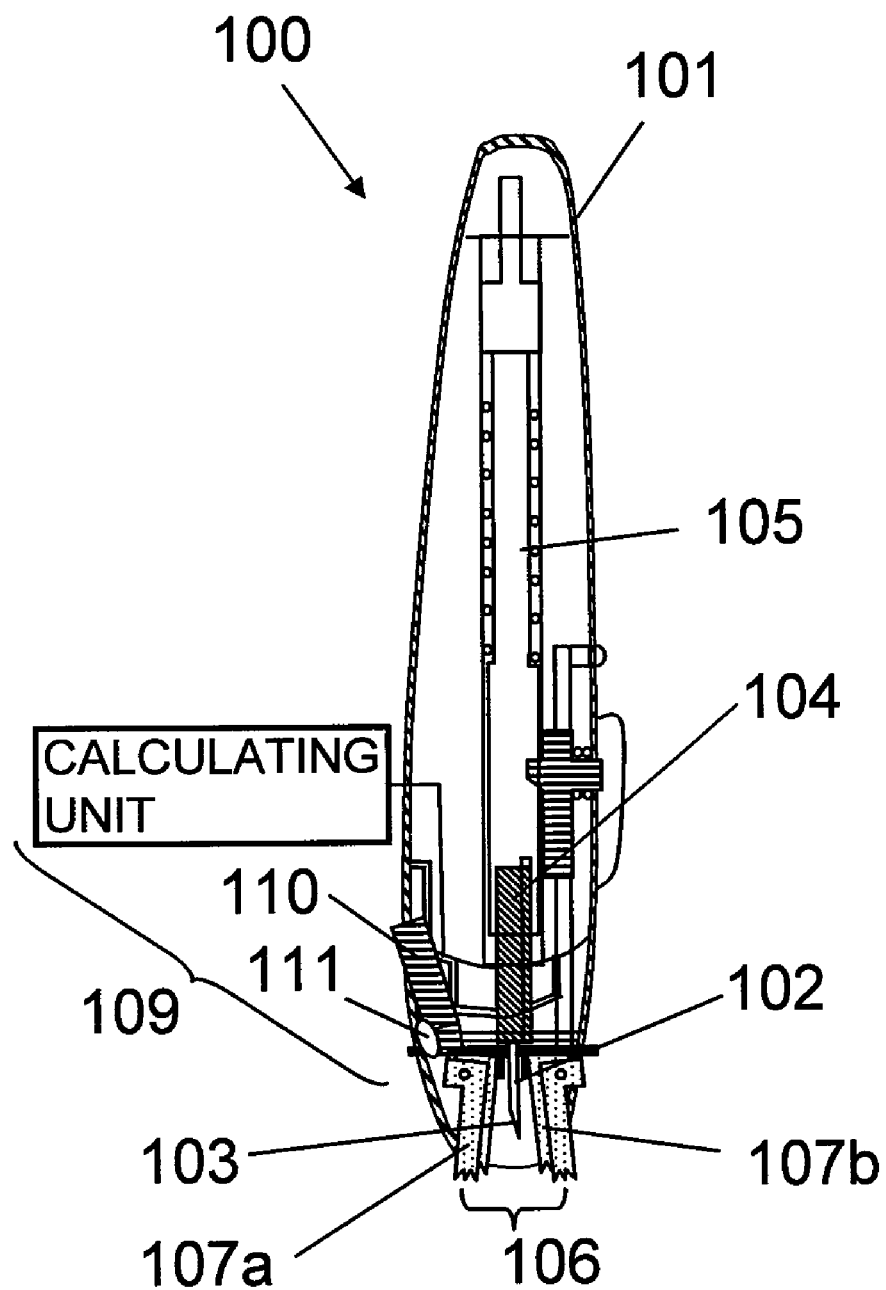
FIG. 1 is a cross-sectional view of the skin incision instrument according to Embodiment of the present invention.
Figure 2:
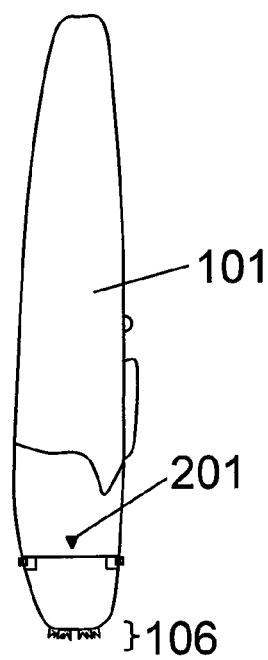
FIG. 2 is an outline view of the skin incision instrument according to Embodiment.

FIG. 1 and FIG. 2 are a cross-sectional view and an outline view of the skin incision instrument according to Embodiment of the present invention, respectively.

In this Embodiment, the skin incision instrument 100 comprises the following elements.

In FIG. 1, the holder 101 comprises an open end and the needle 102 is applied to the skin through the open end. According to the present invention, the size of the holder 101 is not limited. The preferable size of the open end is 5 mm or more and 1 cm or less. According to the present invention, the shape of the holder 101 is not limited. The material of the holder 101 is preferably plastics in view of cost and hygiene standpoint. Polystyrene, polyethylene, vinyl chloride and acryl are preferable.

The needle 102 is mounted at an end of the holder 101. According to the present invention, outer diameter of the needle 102 is not limited. The preferable length of the needle 102 is 500 μm or more and 10 mm or less in view of their strength. The needle 102 does not have to have a uniformly constant outer diameter. The outer diameter may be changed for the needle comprising thin tip and thick root. Then, most preferably, cross-section of the needle 102 except for the tip portion is a round shape, however, polygonal shape such as triangle or diamond shape may also be employed. The needle 102 may be hollow or solid. The material for the needle 102 is preferably austenite stainless, and SUS304 is most preferable, but SUS316 and SUS321 may also be used. Preferable number of the needle 102 is one, but plural needles may also be used. When the plural needles 102 are arranged, blade surfaces thereof are preferably arranged to direct to one direction.

The blade surface 103 is mounted at an end of the needle 102. The incision portion is formed at peripheral surface of skin by mounting the blade surface 103. The most preferable shape of the blade surface 103 is Lancet Point. The applicable shape of the blade surface 103 may include Back-Cut Point, K3-Semi Lancet Point, Flat Dull Bevel, Lancet Bent Tip and Tri Stair Point.

The support 104 is mounted at the other end of the needle 102. By mounting the support 104 onto the other end of the needle 102, the needle 102 is capable of smoothly being mounted to the holder 101. According to the present invention, the size of the support 104 is not limited. According to the present invention, the shape and the material of the support 104 are not limited. To avoid a break of the needle 102 at the tapping thereof, it should preferably be rigid. Applicable shapes of the support 104 may include columnar form, prismatic form, conical form and pyramidal form, and any form which is similar to these forms may also be applicable. The preferable material of the support 104 is plastic. Plastics may include polyethylene, polypropylene, vinyl chloride, polyethylene terephthalate, polystyrene and acryl. The needle 102 and the support 104 are preferably disposable in view of infection prevention. Preferably, the needle 102 and the support 104 are sterilized.

The needle drive unit 105 is mounted in the holder 101. The needle drive unit 105 reciprocates the needle 102 in the longitudinal direction of the holder 101. Reciprocation of the needle 102 allows the needle 102 to tap into the skin and then being removed from the skin. Preferably, the needle drive unit 105 comprises a spring, a connector to the support 104, and an activator.

The skin expander set 106 is mounted at an end of the holder 101. The skin expander set 106 is preferably mounted in the holder 101, but it may be mounted outside the holder 101. An end of the skin expander set 106 contacts with the skin, and the expander set 106 expands the incision portion formed by the needle 102. According to the present invention, the size of the skin expander set 106 is not limited. Further, the shape of the skin expander set 106 is preferably tabular, but it may be roller-shaped or rod-shaped. Otherwise, the skin expander set 106 may be formed by remodeling a part of the opening in the holder 101 into a movable element.

Plastic is preferable as the material of the skin expander set 106. Plastic may include polyethylene, polypropylene, vinyl chloride, polyethylene terephthalate, polystyrene, acryl and polyurethane. An elastic material is also applicable as the material of the skin expander set 106. An elastic material may include silicone rubber, synthesized rubber and Viton. A slip stopper may be mounted at the tip of the skin expander set 106. In order to realize such slip stopper, a rough structure may be mounted at the tip, or the tip may be coated with any antislip material.

The skin expander set 106 is capable of expanding the skin at both sides of the incision portion toward the direction which is away from the incision portion. Depending on the surface condition on skin, the direction which is away from the incision portion may be determined. The surface condition on the skin may be due to the direction of fingerprints, wrinkles, marks of past blood collection, curved surfaces due to bone and tendon, pores or the like.

The reader 109 is mounted at a part of the holder 101. Most preferably, the reader 109 is mounted in the holder 101 and adjacent to an open end thereof. However, it may be mounted outside the holder 101. By mounting the reader 109 at a part of the holder 101, the direction of the incision portion is capable of being read. Then, the position, size and situation of the incision of the incision portion may be read by the reader 109. Pattern recognition may be employed to read the incision portion. The reader 109 comprises preferably the imaging unit 110, the light source 111, and the calculating.

The reader 109 may read the direction of the incision portion in the static condition. Then, the direction of the incision portion may be read in a state where the incision portion is slightly opened. Further, the direction of the incision portion may be read by repeatedly opening and closing the incision portion. In order to open and close the incision portion, it is preferable to employ the skin expander set 106.

A microscope is preferable as the imaging unit 110. By employing a microscope as the imaging unit 110, a fine incision portion can clearly be imaged. It is preferable that magnification of the microscope can be changed, in particular, magnification of 25 times or more and 2500 times or less are preferable. As the imaging unit 110, CCD (Charge-Coupled Device) or CMOS Image Sensor may be employed. As pixel in CCD, 900,000 pixels or more and 10,000,000 pixels or less are preferable. When the imaging unit 110 is CCD, colorific mode of the imaging unit 110 may be color or black-and-white. It is preferable to convert pictures of fine incision portion into digital signals with the CCD, but they may be converted into analog signals. One or more of the imaging unit 110 may be employed. When plural imaging units 110 are employed, same kind of the unit or multiple kinds of the unit may be employed. An optical filter such as polarized filter, near-infrared filter or neutral filter may be mounted between the imaging unit 110 and the incision portion. For example, by employing the polarized filter, effects of diffusely-reflecting light due to fingerprints, wrinkles or skin hairs are prevented, and then the incision portion can clearly be imaged. According to the present invention, the frame rate of the image is not limited.

A halogen lamp is preferable as the light source 111. However, a light-emitting diode, an organic electroluminescence, a fairy light or the like may also be employed. Since the fine incision portion is illumed by the light source 111, the incision portion can clearly be imaged. The incision portion may directly be illumed with the light source 111, or may be illumed thought a transmission means such as an optical fiber or an optical waveguide. Condenser lens may be mounted between the light source 111 and the incision portion. Although it is most preferable to light the incision portion with visible light, near-infrared light with wavelength of 770 nm or more and 1,500 nm or less may also be applied. The incision portion may be lighted with white light, monochromatic light or a combination of plural monochromatic light.

One or more of the light sources 111 may be employed. When plural light sources 111 are employed, same kind of the source or multiple kinds of the source may be employed. A polarized filter may be mounted between the light source 111 and the incision portion to prevent diffuse reflection. Then, an optical filter such as a near-infrared filter or a neutral filter may be mounted between the light source 111 and the incision portion. The reader 109 may employ a display to project the incision portion.

Preferably, the calculating unit read the direction of the incision portion based on an image transmitted from the imaging unit 110. The calculating unit may employ pattern recognition, similarity-based image retrieval, or contour definition.

Figure 3:
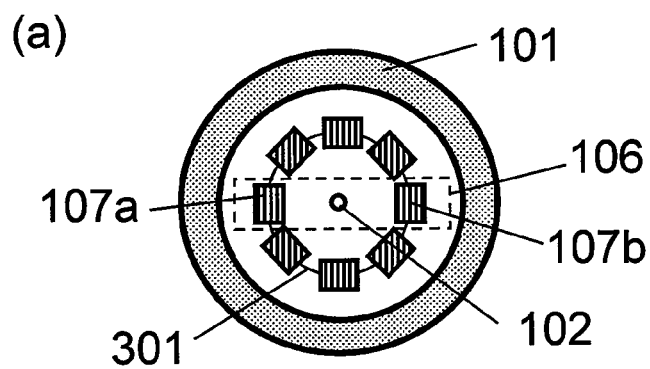
FIG. 3 is a schematic view of the holder viewed from an open end according to Embodiment.
Figure 3:
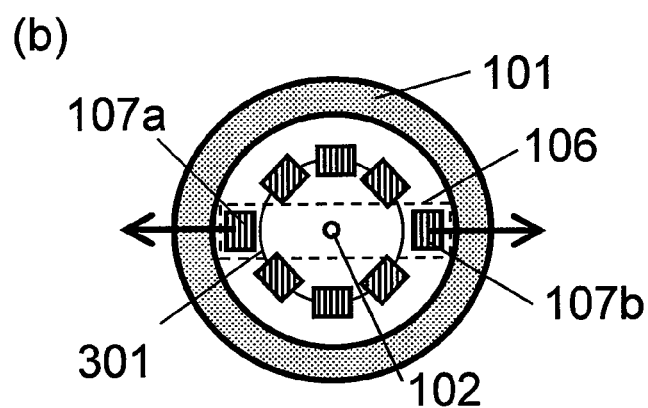

FIGS. 3 (*a*) and (*b*) are schematic views of the holder 101 according to the present Embodiment viewed from the open end thereof. With regard to the elements which are similar to those of FIG. 1 and FIG. 2, the same symbols are applied thereto, and the detailed description thereon is omitted in the present Embodiment.

As illustrated in FIG. 3 (*a*), the skin incision instrument according to the present Embodiment comprises n (n is a natural number of two or more) skin expander sets 106. Each of the skin expander sets 106 comprises the first skin expander 107*a* and the second skin expander 107*b*. The first skin expander 107*a* and the second skin expander 107*b* are preferably mounted around the needle 102 symmetrically. Further, the first skin expander 107*a* and the second skin expander 107*b* are movable away from each other and are capable of expanding the skin by moving them away from each other after contacting the tip thereof with the skin. As illustrated in FIG. 3 (*a*), two or more skin expander sets 106 are preferably mounted around the needle 102 at regular intervals.

A single skin expander set is selected from two or more skin expander sets 106 based on the direction of the incision portion read by the reader 109, such that an angle is adjusted to 45 degrees or more and 90 degrees or less wherein the angle is formed by the direction of the incision portion and the direction of the skin to be expanded by the skin expander set 106.

However, the number of the skin expander set 106 to be selected is not limited. Namely, small numbers (m, m is a natural number of two or more, and n>m) of skin expander sets 106 may be selected from relatively-large numbers of skin expander sets 106, such that each of angles is adjusted to 45 degrees or more and 90 degrees or less wherein each of the angles is formed by the direction of the incision portion and the direction of the skin to be expanded by each of the skin expander sets 106. For example, two skin expander sets 106 are selected from twenty or more skin expander sets 106, such that each of angles is adjusted to 45 degrees or more and 90 degrees or less wherein each of the angles is formed by the direction of the incision portion and the direction of the skin to be expanded by each of the skin expander sets 106. Preferably, the first skin expander 107*a* and the second skin expander 107*b* move simultaneously, but they may move in order. Namely, the first skin expander 107*a* moves firstly, and the second skin expander 107*b* may then move.

In order to clarify the description, the following description illustrates a case wherein a single skin expander set 106 (i.e., m=1) is selected. As a result thereof, m is a natural number of one or more, and is less than n.

According to the present invention, the size of the skin expander set 106 is not limited. The skin expander set 106 is preferably a plate shape comprising an end acting as a fulcrum point, but it may be a part of a hollow cylindrical shape or a rod shape. Otherwise, the skin expander set 106 may be formed by remodeling a part of the opening in the holder 101 into a movable element. Plastic is preferable as the material of the skin expander set 106. Plastic may include polyethylene, polypropylene, vinyl chloride, polyethylene terephthalate, polystyrene, acryl and polyurethane. An elastic material is also applicable as the material of the skin expander set 106. An elastic material may include silicone rubber, synthesized rubber and Viton.

The skin expander set 106 has a mechanism which expands the skin at both sides of the incision portion away from the incision portion. Most preferably, the mechanism expands the skin at both sides of the incision portion in opposite directions in view of efficiency. Alternatively, the mechanism may expand it in substantially opposite directions. More preferably, according to the surface condition of the skin, the direction away from the incision portion may be determined. The surface condition may be due to the direction of fingerprints, wrinkles, scars of the past blood collection, rough surface due to bone or tendon, or pores.

Figure 4:
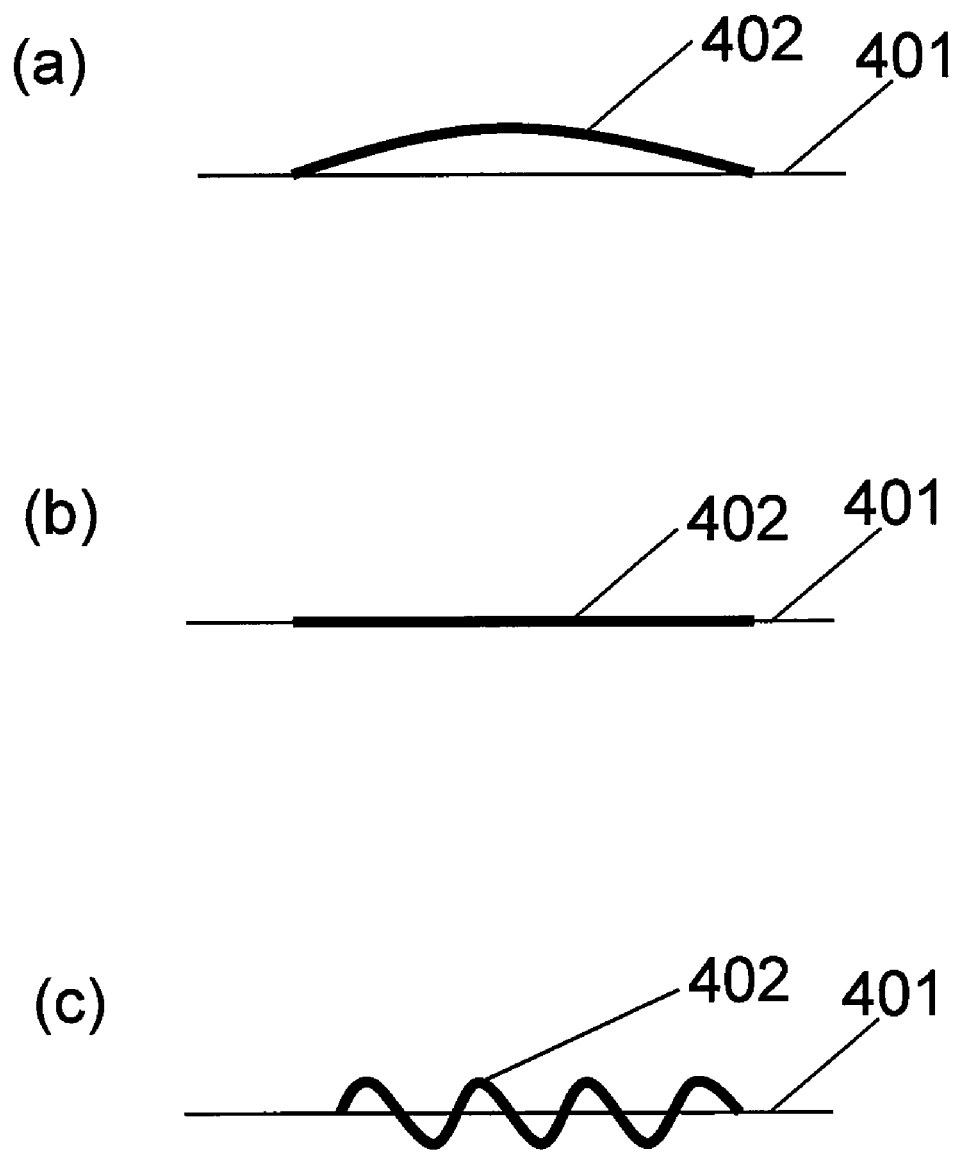
FIG. 4 is a plain view of the incision portion according to Embodiment.

FIGS. 4 (*a*)-(*c*) are plain views of the incision portion. Fingerprints, wrinkles and skin contours are omitted to clarify the description. In FIG. 4 (*a*), the representative line 401 is a straight line which connects both ends of the incision portion 402. The representative line 401 is one of the lines which characterize the direction of the incision portion 402. Representative line 401 is the most convenient simple line which characterizes the incision portion 402. As illustrated in FIGS. 4 (*a*)-(*c*), FIG. 4 (*a*) shows an embodiment wherein the incision portion 402 is a curve line. FIG. 4 (*b*) shows an embodiment wherein the incision portion 402 is a straight line. When the incision portion 402 is a straight line as illustrated in FIG. 4 (*b*), the representative line 401 is substantially corresponding to the incision portion 402. FIG. 4 (*c*) shows an embodiment wherein the incision portion 402 is a wavy line. When the ends of the incision portion 402 are not clear, the points which can be regarded as ends may be connected.

Figure 5:
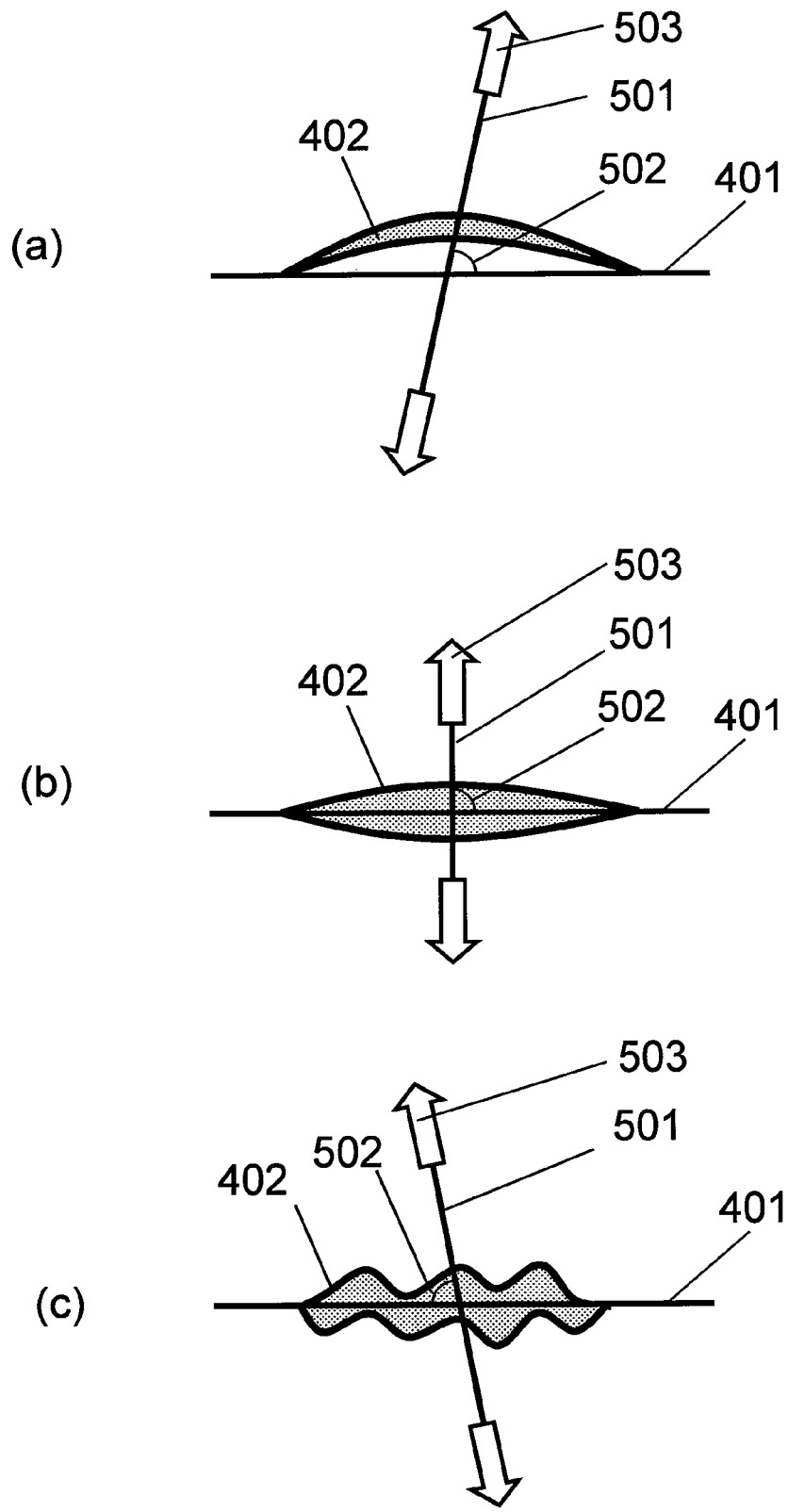
FIG. 5 is an illustrative view showing relationship between the incision portion and the expansion direction of the skin according to Embodiment.

FIGS. 5 (*a*)-(*c*) are illustrative views showing the relationship between the incision portion 402 and the expansion direction of the skin. FIG. 5 (*a*)-(*c*) are elevation views of skin. Fingerprints, wrinkles and skin contours are omitted in order to clarify the description. In FIG. 5 (*a*)-(*c*), the arrow is the force 503 to be applied to the skin.

FIG. 5 (*a*) shows an embodiment wherein the incision portion 402 is curve line. In FIG. 5 (*a*), among the angles formed by the representative line 401 and the line 501 along with expansion direction of skin, a smaller angle is adjusted to 45 degrees or more and 90 degrees or less. Hereinafter, among the angles formed by the representative line 401 and the line 501 along with expansion direction of skin, a smaller angle is called as the expansion angle 502. By adjusting the expansion angle 502 to 45 degrees or more and degrees or less, the incision portion 402 can efficiently be opened. Most preferably, the expansion angle 502 is adjusted to 90 degrees.

FIG. 5 (*b*) shows an embodiment wherein the incision portion 402 is a straight line. In FIG. 5 (*b*), the expansion angle 502 is adjusted to 45 degrees or more and 90 degrees or less. By adjusting the expansion angle 502 to 45 degrees or more and 90 degrees or less, the incision portion 402 can efficiently be opened. Most preferably, the expansion angle 502 is adjusted to 90 degrees.

FIG. 5 (*c*) shows an embodiment wherein the incision portion 402 is a wavy line. In FIG. 5 (*c*), the expansion angle 502 is adjusted to 45 degrees or more and 90 degrees or less. By adjusting the expansion angle 502 to 45 degrees or more and 90 degrees or less, the incision portion 402 can efficiently be opened. Most preferably, the expansion angle 502 is adjusted to 90 degrees.

Two or more skin expander sets 106 allow the skin can be expanded in the direction in which the incision portion can be opened efficiently. Namely, the expansion angle 502 shown in FIG. 5 is easily adjusted to 45 degrees or more and 90 degrees or less.

The operation procedure of the skin incision instrument according to the present embodiment is as follows. FIGS. 6-11 are illustrative views showing the operation procedure of the skin incision instrument. According to the present embodiment, with regard to the elements which are similar to those of FIG. 1 and FIG. 2, the same symbols are applied thereto, and the detailed description thereon is omitted in the present Embodiment.

Figure 6:
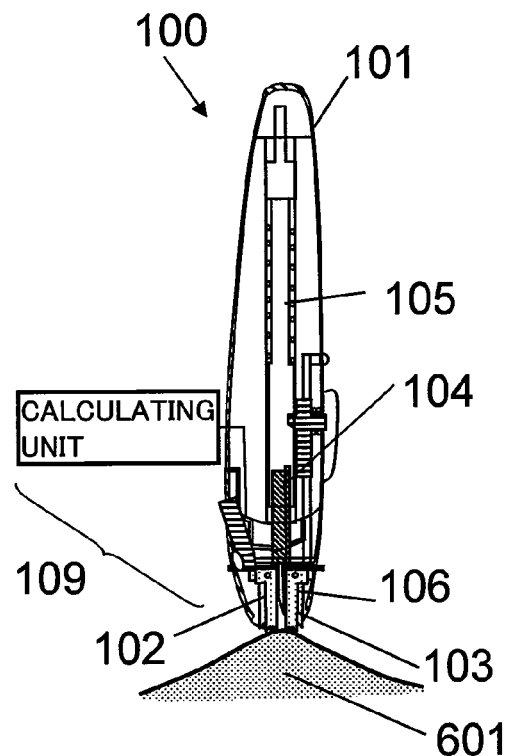
FIG. 6 is an illustrative view showing the skin incision instrument according to Embodiment.

First of all, the skin incision instrument 100 is contacted with skin. FIG. 6 is an illustrative view showing the contact of the skin incision instrument 100 with the skin 601. The open end of the holder 101 preferably contacts with the skin. Prior to the contact of the open end of the holder 101 with skin, the needle 102 and the support 104 are preferably mounted in advance to the holder 101. Further, the fixed direction of the blade surface 103 mounted at an end of the needle 102 is preferably kept against the holder 101.

Figure 7:
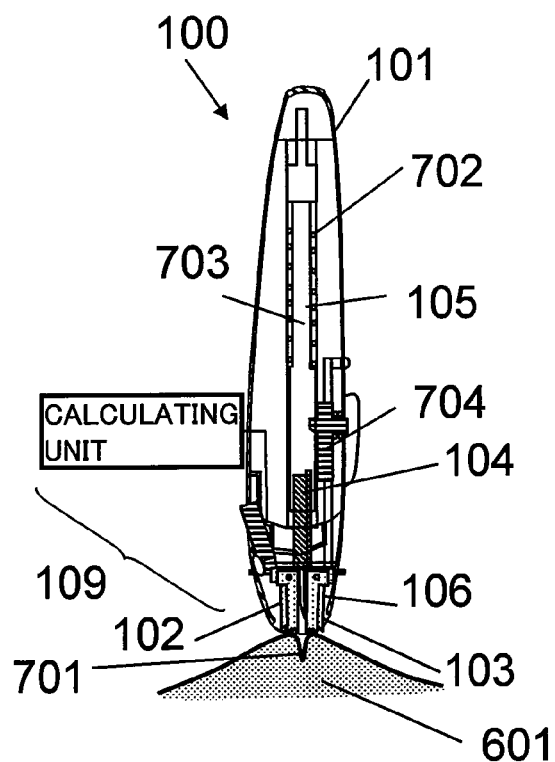
FIG. 7 is an illustrative view showing formation of the incision portion according to Embodiment.

Then, the incision portion 701 is formed onto the skin 601 by the needle 102 with the needle drive unit 105. FIG. 7 is an illustrative view showing that the incision portion 701 is formed onto the skin 601 with the needle 102 and the needle 102 is removed from the skin. The needle drive unit 105 comprises preferably the spring 702, the connector 703 to the support 104, and the activator 704. The needle 102 is preferably reciprocated with elastic force of the spring 702, but the other method may also be employed. Then, when the incision portion 701 is formed onto the skin 601, the skin 601 may be expanded in advance with the skin expander set 106. When the skin 601 is expanded in advance, most preferably, the skin 601 is expanded to the direction which is the vertical direction to the blade surface and is away from the incision portion 701.

Figure 8:
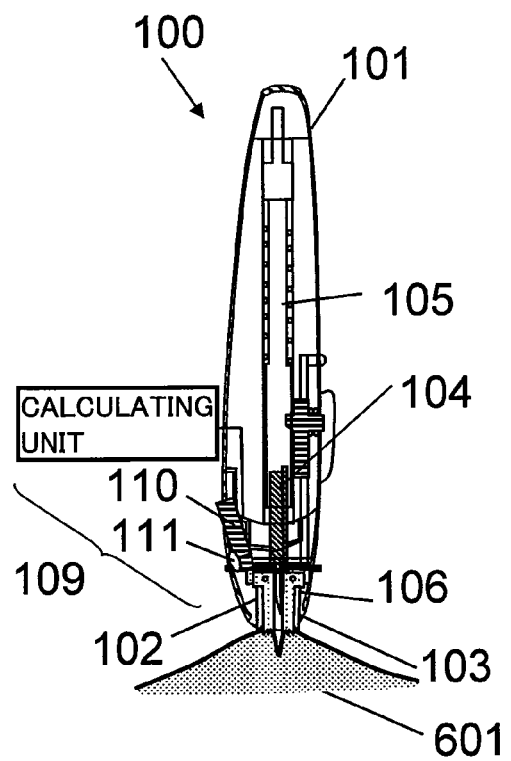
FIG. 8 is an illustrative view showing readout of the incision portion according to Embodiment.

Further, the direction of the incision portions 402 and 701 is read by the reader 109. FIG. 8 is an illustrative view showing that the incision portions 402 and 701 are read by the reader 109. Most preferably, the direction of the incision portions 402 and 701 is determined with the representative line 401 connecting both ends of the incision portions 402 and 701, but the other line may also be employed. In order to read both ends of the incision portions 402 and 701, image recognition such as pattern recognition and contour definition may be used, but the other methodologies may also be employed. The representative line 401 is preferably determined with the calculating unit. Then, when the incision portions 402 and 701 are read, the incision portions 402 and 701 may slightly be opened by the skin expander set 106. By slightly opening the incision portions 402 and 701, both ends of the incision portions 402 and 701 can smoothly be read. When the direction of the incision portions 402 and 701 is read, the direction of the blade surface 103 may be referred to.

Figure 9:
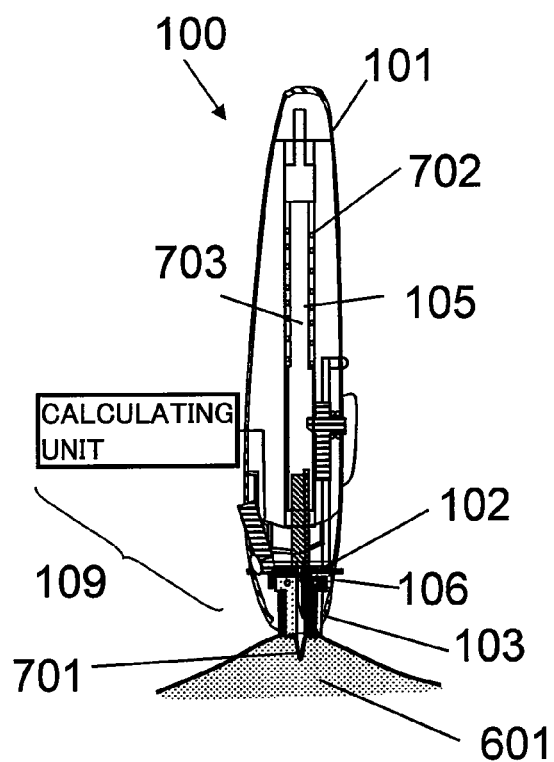
FIG. 9 is an illustrative view showing selection of the skin expander set according to Embodiment.

It is preferable to select a single skin expander set from the skin expander sets 106 based on the direction of the incision portions 402 and 701 read by the reader 109, such that the expansion angle 502 is adjusted to 45 degrees or more and 90 degrees or less. To install two or more skin expander sets 106 is preferable, and to install three or more skin expander sets 106 is more preferable. FIG. 9 is an illustrative view showing the selection of the skin expander set 106. The selected skin expander set 106 is blacked out therein.

The selection of the skin expander set 106 is performed with a manual, an automatic or a semiautomatic operation. When the skin expander set 106 is selected with an automatic or a semiautomatic operation, the calculating unit selects the skin expander set 106 which corresponds to the incised direction determined based on the direction of the incision portion 402.

Figure 10:
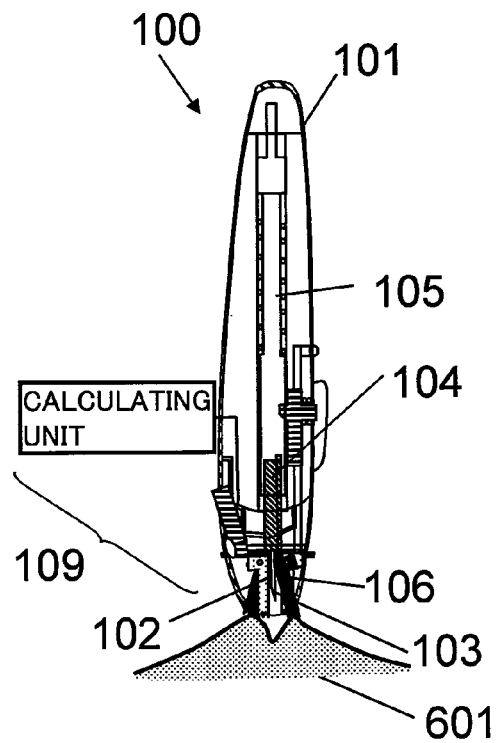
FIG. 10 is an illustrative view showing expansion of skin according to Embodiment.

Further, the skin 601 is expanded with the selected skin expander set in the direction which is away from the incision portion. By expanding the skin 601 in consideration of the direction of the incision portion 701, the incision portion 701 of the various directions can smoothly be opened. When a single skin expander set is selected from two or more skin expander sets 106, it is preferable to separate the other skin expander sets from the skin. FIG. 10 is an illustrative view showing the expansion of the skin with the skin expander set 106.

Figure 11:
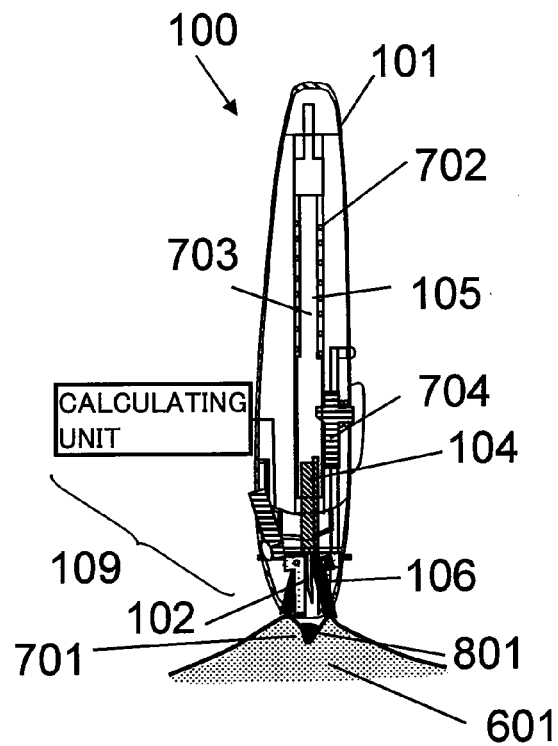
FIG. 11 is an illustrative view showing collection of blood from the incision portion according to Embodiment.

Finally, the blood 801 is collected from the opened incision portion 701. Most preferably, the blood to be collected is exuded naturally from the incision portion 701. This is to prevent the contamination of the tissue fluid and hemolysis. In order to promote the blood collection, as taught by the prior arts, inside of the holder 101 may be depressurized. The skin 601 may be stimulated by moving vertically the holder 101, or the other additional means may also be employed. It is preferable to keep the expansion state of the skin 601 with the skin expander set 106 during at least the collection of the blood 801. Then the reader 109 may be used to detect the collection of the blood. FIG. 11 is an illustrative view showing the collection of blood from the incision portion 701.

According to the foregoing operation procedure, since the skin can be expanded depending on the direction of the incision portion 701, the incision portions 701 can efficiently be formed even if the direction of the incision portion 701 is changed variously.

In the present embodiment, the skin expander set 106 preferably operates in association with the reader 109. Namely, it is preferable that, upon reading the direction of the incision portion 701 by the reader 109, the skin expander set 106 forms the incision portion 701. It is preferable that, upon reading the direction of the incision portion 701 by the reader 109, a signal is duly produced. It is preferable to move the skin expander set 106 according to such signal. Adjustment of the expansion direction of the skin is preferably performed with the calculating unit.

Then, in the present embodiment, it is preferable that the reader 109 operates in association with the skin expander set 106 to read the representative line 401. Since the incision portion 701 is only a line at the closing state thereof, it is not easy to read the incision portion 701 due to fingerprints, wrinkles and pores. Under such circumstances, by slightly opening in advance the incision portion 701 with the skin expander set 106, the position and the direction of the incision portion 701 can be read smoothly. When the incision portion 701 is slightly formed in advance with the skin expander set 106, the skin can be expanded to any direction in the first step. If the incision portion 401 is not being formed in the first step, the skin may be expanded after the skin expander set 106 is rotated around the needle 102 as the second step. Since the skin is expanded to the direction which is different from that in the first step, the incision portion 701 can be formed. In the second step, most preferably, the skin expander set 106 is rotated 90 degrees from the position of the skin expander set 106 in the first step. However, the other angles may also be employed. Then, it is preferable for the reader 109 to indicate on a display the representative line 401 and the expansion direction of skin. Such display method may be realized with an image, numerical numbers, a display bar or the other indication method.

Then, in the present embodiment, the holder 101 may comprise a mark which indicates the direction of the blade surface 103. By indicating the direction of the blade surface 103, it is helpful for the reader 109 to read the direction of the incision portion 701. The mark 201 illustrated in FIG. 2 indicates the blade direction of the fine needle 102 with 200 μm or less. It is preferable to make the mark 201 onto the peripheral surface of the holder 101. The mark 201 may be printed or be molded onto the peripheral surface of the holder 101. Then the mark 201 may be visualized through a transparent window installed at a part of the peripheral surface of the holder 101. The needle 102 and the support 104 may comprise the mark which indicates the direction of the blade surface 103. A particular direction of the blade surface 103 to the holder 101 may be kept. Further, according to the present invention, the shape, the number, the size and the material of the mark 201 are not limited.

Further, in the present embodiment, the skin incision instrument 100 is preferably employed in a blood test kit. A blood glucose test is preferable as the blood test. A Blood test may include a biochemical test on lactic acid, pH, creatinine and urea nitrogen, or a hematological test on hematocrit, hemoglobin and blood count. The other test on immunity, DNA, tumor, allergy or the like may also be applicable.

According to the foregoing elements, since the direction of the incision portion and the direction to expand the skin can easily be adjusted, the incision portions can efficiently be opened even if the direction of the incision portion is changed variously.

EXAMPLES

The operation procedure on the skin incision instrument according to the present invention is as follows.

The holder 101 was made of plastics and was produced in the form of a pen. The length thereof was 12 cm and the diameter thereof was 2 cm.

Figure 12:
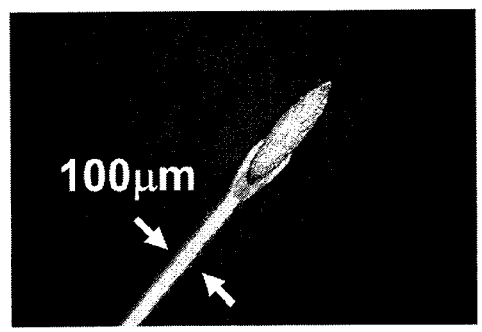
FIG. 12 is an enlarged view showing the needle according to Example.

The needle 102 was made of stainless hollow tube with an outer diameter of 100 μm. With regard to a part where the naked peripheral surface of the needle 102 was appeared, the length thereof was 3 mm. The full length of the needle 102 was 10 mm. SUS304 was employed as a stainless. The cross-section of the needle 102 was a round shape. The inner surface of the needle 102 was smoothed with polishing. FIG. 12 shows an enlarged view of the needle 102. The tip of the needle 102 was covered with a protecting cap until use. The protecting cap was made of polyethylene.

The blade surface 103 was mounted at an end of the needle 102. The shape of the blade surface 103 was Lancet point.

Figure 13:
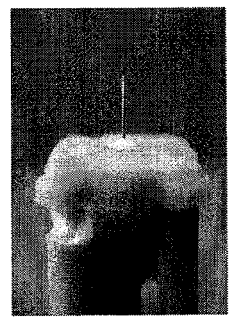
FIG. 13 is an enlarged view showing the support equipped with the needle according to Example.
Figure 14:
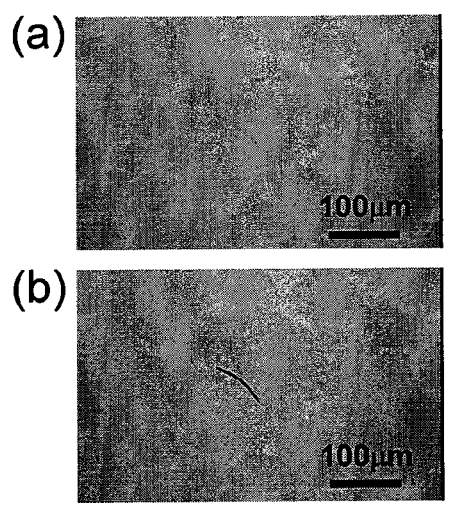
FIG. 14 is an enlarged view showing the incision portion according to Example.
Figure 15:
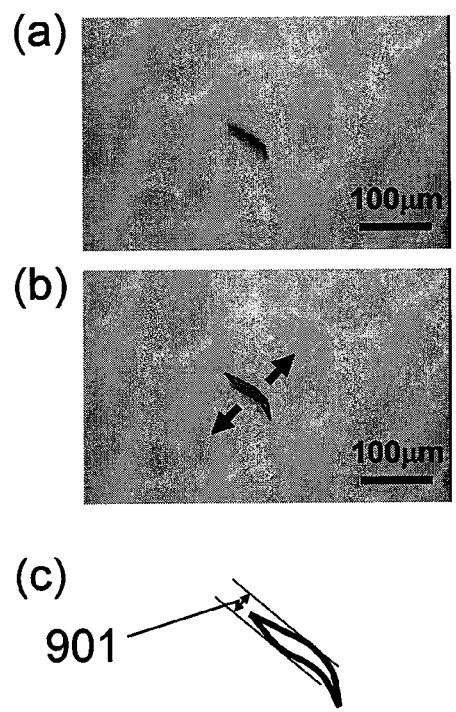
FIG. 15 is an enlarged view showing the incision portion according to Example.
Figure 16:
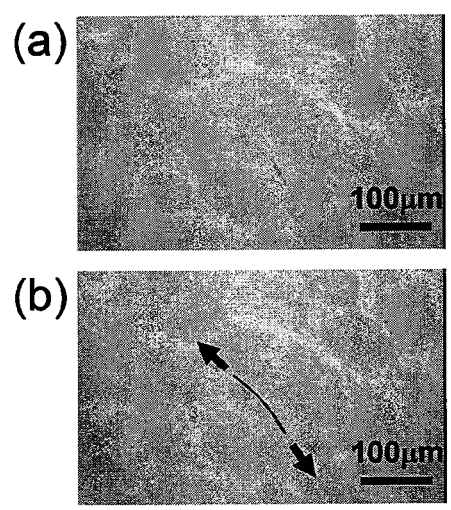
FIG. 16 is an enlarged view showing the incision portion according to Example.
Figure 17:
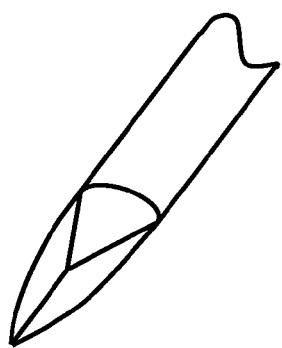
FIG. 17 is a schematic view showing the conventional needle for puncture use.
Figure 18:
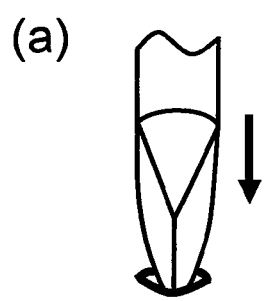
FIG. 18 is an illustrative view showing formation of the incision portion.
Figure 18:
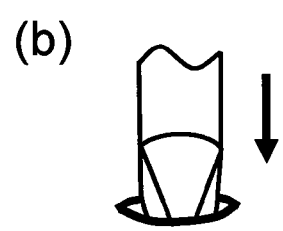
Figure 18:
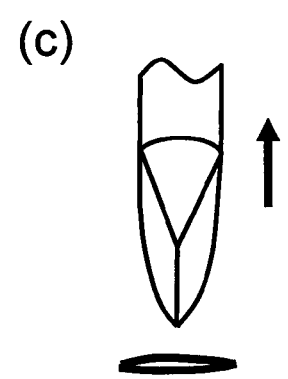
Figure 19:
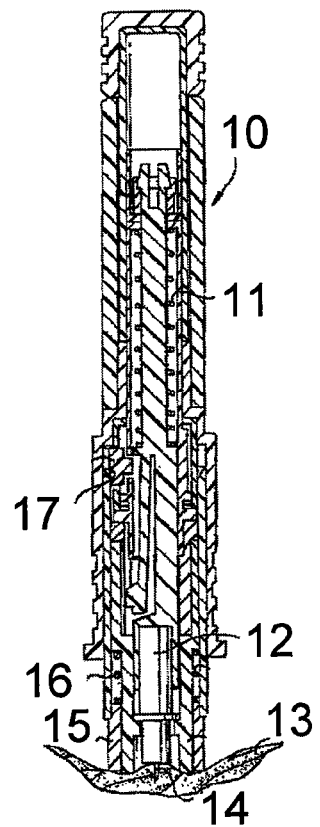
FIG. 19 is an overall view of the conventional skin incision instrument.
Figure 20:
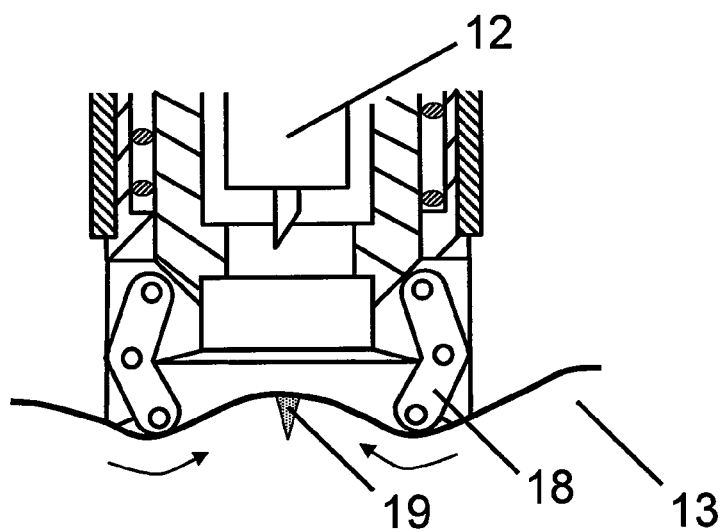
FIG. 20 is an enlarged view of the conventional skin incision instrument.

The support 104 was mounted at the other end of the needle 102. Support 104 was made from polyethylene. The size of the support was 5 mm of width, 5 mm of depth and 22 mm of length. With regard to a part where the needle 102 was naked, the length thereof was 6 mm. The blade surface 103 was mounted on the support 104 by keeping the particular direction thereof. The support 104 had a mark which indicated the direction of the blade surface 103. The support 104 and the protecting cap were produced through integral molding. The support 104 and the needle 102 were subjected to gamma-ray sterilization. Such sterilization can be performed according to the conventional methodology. FIG. 13 is an enlarged view showing the support 104 equipped with the needle 102. The blade surface 103 is directed to the left side of the plane of FIG. 13.

The needle drive unit 105 was mounted in the holder 101. The needle drive unit 105 drove an activator comprising a spring and a connector to the support 104 and the like, and then drove the needle 102 with the spring, and formed the incision portion.

The direction of the incision portion was read with the reader 109. A color CCD camera of 900,000 pixels was employed as the reader 109. An objective lens was mounted in front of the CCD camera, and then the incision portion was enlarged and the image thereof was taken. A halogen lamp was employed as a light source. Light emitted from the halogen lamp was guided with an optical fiber and it irradiated the incision portion. A picture of the incision portion was calculated with the calculating unit, and the direction of the incision portion was read.

Two skin expander sets 106 were installed. Two skin expander sets 106 were mounted around the needle 102 symmetrically. Then the skin expander sets 106 were mounted around the needle 102 at regular intervals.

The skin was expanded with a single skin expander set 106 to adjust the expansion angle 502 to 45 degrees or more and 90 degrees or less. The expansion angle 502 of 90 degrees is most preferable. Further it is preferable to apply extension force to the incision portion in order to realize the opening size thereat of 10 μm or more and 100 μm or less.

The skin incision instrument according to the present invention was applied to an artificial skin. Such artificial skin allows the character of the opening at the incision portion to be determined under the substantially equivalent condition. As an artificial skin, silicone rubber fragment of 20 mm width, 20 mm length and 500 μm thickness was used.

Silicone rubber has usually been used in needle punch experiments. Young's modulus of the silicone rubber used herein was 10 MPa. It is said that Young's modulus of the genuine skin is 0.1-100 MPa.

The opening sizes of each incision portion formed at the expansion angle 502 of 0 degree, 30 degrees, 45 degrees, 60 degrees or 90 degrees were read with the reader 109. Table 1 shows comparison results on the opening sizes at such incision portions. When the opening size so measured was 10 μm or more, the judgment of "◯ (Excellent)" was allocated, and when the opening size was 10 μm or less, the judgment of "x (Unacceptable)" was allocated.

The reason as to why 10 μm of the opening size was employed as a criterion is as follows. The volume of erythrocyte in the blood is about 50% of the blood and the diameter of the erythrocyte is 8 μm. Since the opening size has to be larger than the diameter of the erythrocyte, 10 μm of the opening size was employed as a criterion.

TABLE 1

| Expansion Angle (Degrees) | Judgment |
| --- | --- |
| 0 | x (Unacceptable) |
| 30 | x (Unacceptable) |
| 45 | ◯ (Excellent) |
| 60 | ◯ (Excellent) |
| 90 | ◯ (Excellent) |

As shown in Table 1 above, when the expansion angle 502 was 0 degree or 30 degrees, the opening size of the incision portion was 10 μm or less and was judged as unacceptable. On the other hand, when the expansion angle 502 was 45 degrees, 60 degrees or 90 degrees, the opening size of the incision portion was 10 μm or more and was judged as excellent. When the expansion angle 502 was 90 degrees, the maximum opening size was observed, which was preferable. The similar results were obtained, when the form of the incision portion was a straight line or a wavy line.

According to the foregoing Embodiments, since the skin can be expanded depending on the direction of the incision portion, the incision portions can efficiently be formed even if the direction of the incision portion is changed variously.

INDUSTRIAL APPLICABILITY

Since a skin incision instrument according to the present invention and a method for incising skin with the same expand the skin by reading the direction of the incision portion, the incision portions can efficiently be opened. In particular, blood can easily be taken even if the incision portion is minute. The present invention is useful in the field of home health checkup to determine at home the level of blood glucose, urea nitrogen, creatinine, and blood gas concentration. The present invention is also useful in the field of clinical assay in clinic and hospital. Further, the present invention is applicable to newborns and infants from whom it is difficult to collect the large amount of blood. In addition thereto, the present invention is also applicable to the fields of sports science, police and labor environmental health.

| [Reference Signs List] | |
| --- | --- |
| 10 | incision instrument |
| 11 | compression spring |
| 12 | Lancet |
| 13 | skin |
| 14 | needle |
| 15 | cylindrical ring |
| 16 | coil spring |
| 17 | trigger |
| 18 | lever |
| 19 | incision portion |
| 100 | skin incision instrument |
| 101 | holder |
| 102 | needle |
| 103 | blade surface |
| 104 | support |
| 105 | needle drive unit |
| 106 | skin expander set |
| 107a | first skin expander |
| 107b | second skin expander |
| 109 | reader |
| 110 | imaging unit |
| 111 | light source |
| 201 | mark |
| 301 | axis line |
| 401 | representative line |
| 402 | incision portion |
| 501 | line in expansion direction of skin |
| 502 | expansion angle |
| 503 | force to be applied to skin |
| 601 | skin |
| 701 | incision portion |
| 702 | spring |
| 703 | connector |
| 704 | activator |
| 801 | blood |
| 901 | opening size |

The invention claimed is:

1. A method for incising skin with a skin incision instrument the method comprising steps of:
   incising, utilizing a driving unit of the skin incision instrument and a needle of the skin incision instrument, to form a incision portion in the skin;
   reading, utilizing a reader of the skin incision instrument, a direction of the incision portion;

selecting m skin expander set(s) from n skin expander sets, based on the direction of the incision portion read by the reader, the m skin expander set(s) configured to form an angle between 45° and 90, wherein the angle is formed by the direction of the incision portion in the reading step and the direction to expand the skin by the m skin expander set(s); and expanding, utilizing the m expander set(s), to expand the skin at both sides of the incision portion away from the incision portion;

wherein the selecting step is performed by a calculating unit.

2. The method of claim 1, wherein, m is a natural number of one or more and n is a natural number of two or more, and n is greater than m.

3. The method according to claim 2, wherein m is one.

4. The method of claim 1, wherein, the m skin expander set(s) comprise a first skin expander and a second skin expander.

5. The method of claim 4, wherein, the first skin expander and the second skin expander are positioned symmetrically around an axis defined by the needle.

6. The method of claim 1, wherein the needle is mounted on end of a holder of the skin incision instrument.

7. The method of claim 1, wherein the incision portion is linear.

8. The method according to claim 1, wherein the incising step, the reading step, the selecting step, and the expanding step are performed in this order.

* * * * *